(12) United States Patent
Kocur et al.

(10) Patent No.: US 8,475,844 B2
(45) Date of Patent: Jul. 2, 2013

(54) FLUOROPOLYMER-BASED MEDICAL IMPLANT COATING COMPOSITIONS

(75) Inventors: Gordon Kocur, Lino Lakes, MN (US); David Rolf, Eden Prairie, MN (US); James Lasch, Oakdale, MN (US); Kasyap Seethamraju, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 365 days.

(21) Appl. No.: 12/424,946

(22) Filed: Apr. 16, 2009

(65) Prior Publication Data
US 2009/0264539 A1 Oct. 22, 2009

Related U.S. Application Data

(60) Provisional application No. 61/045,331, filed on Apr. 16, 2008.

(51) Int. Cl.
*A61K 9/14* (2006.01)

(52) U.S. Cl.
USPC .......................................................... 424/487

(58) Field of Classification Search
None
See application file for complete search history.

(56) References Cited

U.S. PATENT DOCUMENTS

| | | | | |
|---|---|---|---|---|
| 4,023,995 A * | 5/1977 | Reed et al. | 149/19.3 |
| 4,125,673 A * | 11/1978 | Roth et al. | 428/447 |
| 4,348,312 A * | 9/1982 | Tung | 428/144 |
| 4,366,299 A * | 12/1982 | Dessaint | 526/243 |
| 4,701,508 A * | 10/1987 | Homma et al. | 526/249 |
| 4,920,190 A * | 4/1990 | Lina et al. | 526/243 |
| 5,024,507 A * | 6/1991 | Minns et al. | 385/145 |
| 5,144,056 A * | 9/1992 | Lina et al. | 560/25 |
| 5,147,938 A * | 9/1992 | Kuller | 525/276 |
| 5,216,097 A * | 6/1993 | Allewaert et al. | 526/243 |
| 5,344,956 A * | 9/1994 | Allewaert et al. | 560/56 |
| 5,446,118 A * | 8/1995 | Shen et al. | 526/245 |
| 5,705,583 A * | 1/1998 | Bowers et al. | 526/277 |
| 5,965,256 A * | 10/1999 | Barrera | 428/354 |
| 6,025,092 A * | 2/2000 | Doyle et al. | 429/213 |
| 6,028,163 A * | 2/2000 | Zhao | 528/340 |
| 6,090,492 A * | 7/2000 | Tsuchiya et al. | 428/421 |
| 6,280,878 B1 * | 8/2001 | Maruyama et al. | 429/233 |
| 6,475,663 B1 * | 11/2002 | Mohwald et al. | 429/129 |
| 6,551,708 B2 * | 4/2003 | Tsuda et al. | 428/402 |
| 6,586,530 B1 * | 7/2003 | Goetz et al. | 525/227 |
| 6,773,815 B2 * | 8/2004 | Amouroux | 428/418 |
| 6,803,419 B2 * | 10/2004 | Tsuda et al. | 525/197 |
| 6,902,839 B2 * | 6/2005 | Park et al. | 429/492 |
| 7,211,352 B2 * | 5/2007 | Lee et al. | 429/309 |
| 7,244,443 B2 * | 7/2007 | Pacetti | 424/423 |
| 7,291,369 B2 * | 11/2007 | Fukushi | 428/35.7 |
| 7,291,688 B2 * | 11/2007 | Qiu et al. | 526/242 |
| 7,294,376 B2 * | 11/2007 | Zanzig | 428/36.8 |
| 7,399,556 B2 * | 7/2008 | Lee et al. | 429/309 |
| 2002/0084382 A1 * | 7/2002 | Crist | 244/134 B |
| 2003/0096929 A1 * | 5/2003 | Olson et al. | 526/243 |
| 2003/0100675 A1 * | 5/2003 | Goetz et al. | 525/88 |
| 2003/0104213 A1 * | 6/2003 | Halladay et al. | 428/421 |
| 2003/0207118 A1 * | 11/2003 | Fukushi | 428/421 |
| 2003/0219604 A1 * | 11/2003 | Yamamoto et al. | 428/421 |
| 2003/0224235 A1 * | 12/2003 | Park et al. | 429/33 |
| 2004/0059408 A1 | 3/2004 | Alvarado | |
| 2004/0176556 A1 | 9/2004 | Bowers et al. | |
| 2004/0185267 A1 * | 9/2004 | Takahashi et al. | 428/423.1 |
| 2004/0214089 A1 * | 10/2004 | Lee et al. | 429/309 |
| 2005/0106203 A1 | 5/2005 | Roorda et al. | |
| 2005/0106204 A1 | 5/2005 | Hossainy et al. | |
| 2005/0150172 A1 * | 7/2005 | Sato | 51/298 |
| 2005/0196677 A1 * | 9/2005 | Lee et al. | 429/309 |
| 2006/0013854 A1 | 1/2006 | Strickler et al. | |
| 2006/0047095 A1 | 3/2006 | Pacetti | |
| 2006/0142518 A1 * | 6/2006 | Qiu et al. | 526/319 |
| 2006/0165919 A1 | 7/2006 | Suzuki et al. | |
| 2006/0228604 A1 * | 10/2006 | Huang | 429/30 |
| 2007/0117925 A1 | 5/2007 | Strickler | |
| 2008/0008736 A1 * | 1/2008 | Glauser | 424/423 |
| 2008/0071021 A1 * | 3/2008 | Qiu et al. | 524/537 |

FOREIGN PATENT DOCUMENTS

| | | | |
|---|---|---|---|
| EP | 0243605 A2 | 11/1987 |
| EP | 0765890 A2 | 4/1997 |
| JP | 11155944 A | 6/1999 |
| WO | 2005049678 A2 | 6/2005 |

OTHER PUBLICATIONS

Li-Piin Sung, Silvia Vicini, Derek L. Ho, Lotfi Hedhli, Christyn Olmstead, Kurt A. Wood. Effect of microstructure of fluorinated acrylic coatings on UV degradation testing. Polymer 45 (2004) 6639-6646.*
Natany M.L. Hansen, Katja Jankova and Søren Hvilsted. Fluoropolymer materials and architectures prepared by controlled radical polymerizations. European Polymer Journal vol. 43, Issue 2, Feb. 2007, pp. 255-293.*
Akira Shimotoyodome, et al. Reduction of *Streptococcus mutans* Adherence and Dental Biofilm Formation by Surface Treatment with Phosphorylated Polyethylene Glycol. Antimicrob. Agents Chemother. Oct. 2007 vol. 51 No. 10 3634-3641.*
Hu Yan Dr., Hideki Fujiwara Dr., Keiji Sasaki Prof. Dr., Kaoru Tsujii Prof. Dr. Rapid Swelling/Collapsing Behavior of Thermoresponsive Poly(N-isopropylacrylamide) Gel Containing Poly(2-(methacryloyloxy)decyl phosphate) Surfactant. Angewandte Chemie (2005) vol. 117, Issue 13, pp. 1987-1990.*
V.C. Malshe, Nivedita S. Sangaj. Fluorinated acrylic copolymers. Part I: Study of clear coatings. Progress in Organic Coatings 53 (2005) 207-211.*

(Continued)

*Primary Examiner* — Robert A Wax
*Assistant Examiner* — Olga V Tcherkasskaya
(74) *Attorney, Agent, or Firm* — Mayer & Williams PC; David B. Bonham

(57) ABSTRACT

Polymers of fluorinated monomers and acrylate and alkyl acrylates are disclosed which demonstrate improved performance as coatings for implantable devices. Such coatings may, for example, be used to release a bioactive agent from the medical device. One specific application lies in drug-eluting coatings for stents.

31 Claims, No Drawings

OTHER PUBLICATIONS

V C Malshe, S. Elango, S.S. Bhagwat, S.S. Maghrabi. Fluorinated acrylic copolymers Part II: Polymeric surfactants. Progress in Organic Coatings 53 (2005) 212-216.*

Masamichi Morita, Hiroko Ogisu, Motonobu Kubo. Surface Properties of Perfluoroalkylethyl Acrylate/n-Alkyl Acrylate Copolymers. Journal of Applied Polymer Science, vol. 73, 1741-1749 (1999).*

Akira Hirao,, Kenji Sugiyama, Hideaki Yokoyama. Precise synthesis and surface structures of architectural per - and semifluorinated polymers with well-defined structures. Prog. Polym. Sci. 32 (2007) 1393-1438.*

BIMAX Products, 2-Hydroxyethyl methacrylate [online] Bimax Chemicals Ltd., Jun. 18, 2006 [retrieved on Jun. 4, 2009] Retrieved from the Internet: <URL:http://www.bimax.com/hema.htm>. (teaches structure of hydroxyethyl methacrylate).

International Search Report issued Jun. 11, 2009 during the prosecution of International Application No. PCT/US2009/40784.

Scott, C.E. PolymerProcessing.com: Information, education, resources and expertise in the field of polymer processing. Polymers[online]. PolymerProcessing.com. Jun. 2001 [retrieved on Jun. 4, 2009). Retrieved from the Internet: <URL:http://www.polymerprocessing.com/polymers/alpha.html>. (teaches structures of ethyl acrylate, ethyl methacrylate, hexyl methacrylate).

Written Opinion issued Jun. 11, 2009 during the prosecution of International Application No. PCT/US2009/40784.

Xue, J. et al., "Stimuli-Responsive Multifunctional Membranes of Controllable Morphology from Poly(vinylidene fluoride)-graft-Poly[2-(N,N-dimethylamino)ethyl methacrylate] Prepared via Atom Transfer Radical Polymerization", Langmuir, vol. 24, No. 24, 2008, pp. 14151-14158, XP002678181, ISSN: 0743-7463.

* cited by examiner

FLUOROPOLYMER-BASED MEDICAL IMPLANT COATING COMPOSITIONS

CROSS-REFERENCE TO RELATED APPLICATIONS

This application claims priority to U.S. provisional patent application Ser. No. 61/045,331, filed Apr. 16, 2008.

BACKGROUND OF THE INVENTION

This invention relates to improved biocompatible polymer compositions. Polymers of fluorinated monomers and alkyl acrylates demonstrate improved performance as coatings for implantable devices. Such coatings may, for example, be used to release a bioactive agent from the medical device. One specific application lies in drug eluting coatings for stents. Although stents have important medical uses, problems of restenosis and thrombosis remain. Pharmacological therapy in the form of a drug-delivery stent appears a feasible means to tackle these biologically derived issues. Polymeric coatings placed onto the stent serve to act both as the drug reservoir, and to control the release of the drug. The nature of the coating polymers plays an important role in defining the surface properties of a coating. For example, a very low $T_g$, amorphous coating material can have unacceptable Theological behavior upon mechanical perturbation such as crimping, balloon expansion, etc. On the other hand, a high $T_g$, or highly crystalline coating material introduces brittle fracture in the high strain areas of the stent pattern.

Some of the currently used polymeric materials such as poly(vinylidene difluoride-co-hexafluoropropene) (PVDF-co-HFP) have good mechanical properties, and acceptable biocompatibility, but also have low permeability to drugs. While PVDF polymers possess excellent characteristics that permit their use in medical device based coatings or articles, one aspect of PVDF polymer that could be a detriment is the low coefficient of surface friction. This is an intrinsic property of the polymer surface. This property could cause problems during stent securement process. Compositions within this disclosure aim at reducing the surface slipperiness or increase the surface friction so coated devices could be handled better. Use of hydrophobic acrylate or methacrylate based copolymer segments with glass transition temperature $T_g$ below −35° C. could be elastomeric and could impart slightly higher friction.

In U.S. 2004/0224001, Pacetti, et al. disclosed a medical implant coating that includes a mixture of a hydrophobic polymer and a polymeric hydrophilic additive, wherein the hydrophobic polymer and the hydrophilic additive form a physically entangled or interpenetrating system. Pacetti, U.S. Pat. No. 7,244,443, and Ding, U.S. 2006/0067908, attempted to address some of the problems in this area through the use of a polymer formed of fluorinated monomers and hydrophilic monomers. The fluorinated monomers were said to provide mechanical strength and/or flexibility, biocompatibility, and physiologic durability for the polymer. Strickler et al., U.S. 2007/0117925, discloses copolymers having at least one fluorocarbon-containing block copolymer, which, in turn, contains (a) at least one fluorocarbon-containing, low glass transition temperature (low $T_g$) copolymer chain and (b) at least one glass transition temperature (high $T_g$) polymer chain. Other similar efforts include U.S. Pat. Nos. 7,175,873; and 7,247,313 to Roorda, et al.; U.S. 2005/0106204 to Hossainy et al.

The present invention is a further improvement by addressing the continuing problems in the art by providing a polymeric material for coating implantable devices.

SUMMARY OF THE INVENTION

The invention provides generally to polymer compositions; more specifically to polymer compositions for elution of drug substances.

In one embodiment, there is a copolymer composition, said copolymer composition comprising: a fluoromonomer unit; and, an acrylate monomer unit selected from the group consisting of acrylate monomer units of formula I, acrylate monomer units of formula II, acrylate monomer units of formula III, and combinations thereof, wherein formulas I, II, and II are herein defined, wherein when $R^1$ is a $C_6$-$C_{10}$ aryl, a 5- to 12-membered heterocyclic group, $C_1$-$C_{10}$ alkyl, $C_2$-$C_{10}$ alkenyl, $C_2$-$C_{10}$ alkynyl, or $C_3$-$C_6$ cycloalkyl; and $R^2$ is hydrogen, a $C_6$-$C_{10}$ aryl, a 5- to 12-membered heterocyclic group, $C_1$-$C_{10}$ alkyl, $C_2$-$C_{10}$ alkenyl, $C_2$-$C_{10}$ alkynyl, or $C_3$-$C_6$ cycloalkyl, and further wherein $R^1$ and $R^2$ may be the same or different.

In some embodiments, the mole % of acrylate is 50% or lower. In some embodiments, the mole % of acrylate is selected from the group consisting of 10-20%, 10-50%, and 25-50%. In some embodiments, the copolymer composition has a glass transition temperature of less than 35° C. In other embodiments, the copolymer composition has a glass transition temperature of less than 20° C. The fluoromonomer unit may be selected from the group consisting of vinylidene difluoride, hexfluoropropylene and combinations thereof in various embodiments.

The copolymer composition may comprise a random copolymer, a block copolymer, or a graft copolymer.

In some embodiments of the copolymer composition, the acrylate monomer unit is selected from the group consisting of methylmethacrylate, ethylmethacrylate, butylmethacrylate, hexylmethacrylate, methacrylate, n-butylacrylate, ethylacrylate, and any combination thereof.

In some embodiments, the copolymer composition further comprises a bioactive agent. One example of such a bioactive agent is an antithrombotic agent.

In some embodiments of the he copolymer composition, the composition further comprises an additional monomer unit wherein the additional monomer unit is present at less than 10 mole % of the composition.

In another embodiment, there is a copolymer composition, said copolymer composition comprising: a fluoromonomer unit; and, an acrylate monomer unit of formula IV, wherein formula IV is herein defined, wherein Y is selected from the group consisting of —COOH, —NH$_2$, —SH, —OH, —Si(OCH$_3$)$_3$, —C(O)NH$_2$, —N(H)C(O)NH$_2$, and —N(H)C(O)OH.

In some embodiments, the fluoromonomer unit is selected from the group consisting of vinylidene difluoride, hexfluoropropylene and combinations thereof. In some embodiments, the mole % of acrylate is 50% or lower. In some embodiments, the mole % of acrylate is selected from the group consisting of 10-20%, 10-50%, and 25-50%. In some embodiments, the copolymer composition has a glass transition temperature of less than 35° C. In other embodiments, the copolymer composition has a glass transition temperature of less than 20° C. In some embodiments, the copolymer composition comprises a random copolymer, a block copolymer, or a graft copolymer.

In some embodiments of the copolymer composition, the composition further comprising a bioactive agent. One example of such a bioactive agent is an antithrombotic agent.

In some embodiments, the copolymer composition further comprises an additional monomer unit wherein the additional monomer unit is present at less than 10 mole % of the composition.

In another embodiment, there is a copolymer composition, the copolymer composition comprising: a fluoromonomer unit; and, an acrylate monomer unit of formula V, formula VI, or a combination thereof, wherein formulas V and VI are herein defined. In some embodiments of the copolymer composition, the fluoromonomer unit is selected from the group consisting of vinylidene difluoride, hexfluoropropylene and combinations thereof. In some embodiments of the copolymer composition, the mole % of acrylate is 50% or lower. In some embodiments of the copolymer composition, the mole % of acrylate is selected from the group consisting of 10-20%, 10-50%, and 25-50%. In some embodiments, the copolymer composition has a glass transition temperature of less than 35° C. In some embodiments, the copolymer composition has a glass transition temperature of less than 20° C. In some embodiments of the copolymer composition, the copolymer is a random copolymer a block copolymer, or a graft copolymer. In some embodiments of the copolymer composition, the copolymer composition further comprises a bioactive agent. One example of such a bioactive agent is an antithrombotic agent. In some embodiments of the copolymer composition, the copolymer composition further comprises an additional monomer unit wherein the additional monomer unit is present at less than 10 mole % of the composition.

In another embodiment, there is a polymer blend composition, the composition comprising a fluoropolymer; and, an polyacrylate having a hydrophobic acrylate monomer unit selected from the group consisting of acrylate monomer units of formula I, acrylate monomer units of formula II, acrylate monomer units of formula III, and combinations thereof, wherein formulas I, II, and II are herein defined, wherein when $R^1$ is a $C_6$-$C_{10}$ aryl, a 5- to 12-membered heterocyclic group, $C_1$-$C_{10}$ alkyl, $C_2$-$C_{10}$ alkenyl, $C_2$-$C_{10}$ alkynyl, or $C_3$-$C_6$ cycloalkyl; and $R^2$ is hydrogen, a $C_6$-$C_{10}$ aryl, a 5- to 12-membered heterocyclic group, $C_1$-$C_{10}$ alkyl, $C_2$-$C_{10}$ alkenyl, $C_2$-$C_{10}$ alkynyl, or $C_3$-$C_6$ cycloalkyl, and further wherein $R^1$ and $R^2$ may be the same or different. In some embodiments of the polymer blend composition, the blend composition further comprises a third polymer, the third polymer being substantially free of fluoromonomers and acrylate monomers.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

As used herein, "a" or "an" may mean one or more. As used herein in the claim(s), when used in conjunction with the word "comprising", the words "a" or "an" may mean one or more than one. As used herein, "another" may mean at least a second or more.

As used herein, a "fluoropolymer" is a polymer that contains at least monomer having one or more atoms of fluorine. Examples include, but are not limited to, polytetrafluoroethylene (PTFE), perfluoroalkoxy polymer resin (PFA), fluorinated ethylene-propylene (FEP), polyethylenetetrafluoroethylene (PETFE), polyvinylfluoride (PVF), polyethylenechlorotrifluoroethylene (PECTFE), polyvinylidene fluoride (PVDF), polychlorotrifluoroethylene (PCTFE), polyhexafluoropropylene (PHFP). The corresponding fluoromonomers are clear from the recited polymers. The term "fluoropolymer" includes homopolymers, copolymers, including random, block, or graft copolymers, as well as terpolymers and higher polymers.

As used herein, the term "mole %" in reference to a specific component means the amount of such component in percent by moles. It is synonymous with "mol %".

As used herein, a "polyacrylate" is a polymer that contains at least monomer having an acrylate moiety, with the term "acrylate" as further defined herein. The term "polyacrylate" includes homopolymers, copolymers, including random, block, or graft copolymers, as well as terpolymers and higher polymers. In the case of copolymers, terpolymers and higher polymers, such polymers may contain one or more than one acrylate monomers and one or more than one non-acrylate monomers. In the broadest sense, the term "acrylate" is a composition comprising formula I (defined herein), however having $R^1$ and $R^2$ constituents not limited to the specific groups described herein. However, the acrylates of the present invention are those limited to the specific $R^1$ and $R^2$ constituents herein described. A polyacrylate is a subset of acrylates.

The term "fluoromonomer unit", when referring to a portion of a copolymer which comprises both fluorine-containing monomers and acrylate-containing monomers, can refer to both a single fluoromonomer (such as hexafluoropropylene) or more than one fluoromonomer (such as vinylidene fluoride and hexafluoropropylene). In cases of more than one fluoromonomer, it should be understood that the relative amounts of each single fluoromonomer can be the same or different and is variable. The term "acrylate monomer unit", when referring to a portion of a copolymer which comprises both fluorine-containing monomers and acrylate-containing monomers, can refer to both a single acrylate monomer (such as n-butyl acrylate) or more than one acrylate monomer (such as n-butyl acrylate and methylmethacrylate). In cases of more than one acrylate monomer, it should be understood that the relative amounts of each single acrylate monomer can be the same or different and is variable.

In certain embodiments, the invention provides a composition that is an inert, low surface energy coating for medical devices that are implanted into the body of a mammal and later retrieved therefrom. The low surface energy coating makes wetting of the device surface and protein deposition thereon difficult, which could prolong the time for encapsulation in the body, after which time the device could be removed easily. In certain embodiments of the invention, although not necessary, the coatings may comprise pharmaceutical or therapeutic agents in amounts effective for achieving desired purposes, e.g., for reducing thrombosis or restenosis, and stents coated with such coatings may provide sustained release of the agents. Films prepared from the compositions of the present invention provide the physical and mechanical properties required of conventional coated medical devices, even where maximum temperatures to which the device, coatings and films are exposed are limited to relatively low temperatures, for example, less than about 100° C., preferably at about ambient temperatures. This is particularly important when using the coating/film to deliver pharmaceutical/therapeutic agent or drugs that are heat sensitive, or when applying the coating onto temperature-sensitive devices such as, but not limited to, catheters. When maximum exposure temperature is not an issue, e.g. where heat-stable agents such as itraconazole are incorporated into the coatings, higher melting thermoplastic polyfluoro copolymers may be used and, if very high elongation and adhesion is required, elastomers may be used. If desired or required, the polyfluoro elastomers may be crosslinked by standard methods described in, e.g., Modern Fluoropolymers, J. Shires editor, John Wiley & Sons, New York, 1997, pp. 77-87.

The present invention comprises polymer compositions that provide improved biocompatible coatings for medical devices. These coatings provide inert surfaces to be in contact with body tissue of a mammal, e.g., a human, sufficient to reduce thrombosis, or restenosis, or other undesirable reactions. While most reported coatings made from polyfluoro homopolymers are insoluble and/or require high heat, e.g. greater than about 125° C., to obtain films with adequate physical and mechanical properties for use on implantable devices, e.g., stents, or are not particularly tough or elastomeric, films prepared from the polyfluoro copolymer coatings of the present invention provide adequate adhesion, toughness or elasticity, and resistance to cracking when formed on medical devices claimed herein. In certain embodiments, this is the case even where the coated devices are subjected to relatively low maximum temperatures, e.g. less than about 100° C., preferably less than about 65° C., and more preferably about 60° C. or less. In certain embodiments, the copolymers will be crystalline, although amorphous copolymers of similar composition also are employed.

The copolymers used for coatings according to the present invention must be film-forming polymers that have molecular weight high enough so as not to be waxy or tacky. The polymers and films formed therefrom must adhere to the stent and not be readily deformable after deposition on the stent as to be able to be displaced by hemodynamic stresses. The polymer molecular weight must be high enough to provide sufficient toughness so that films comprising the polymers will not be rubbed off during handling or deployment of the stent. In certain embodiments the coating will not crack where expansion of the stent or other medical devices, such as vena cava filters, occurs. The flow point of the polymer used in the present invention should be above 40° C., preferably above about 45° C., more preferably above 50° C. and most preferably above 55° C.

Conventional polyfluoro homopolymers used for medical implants are crystalline and difficult to apply as high quality films onto metal surfaces without exposing the coatings to relatively high temperatures that correspond to the melting temperature (Tm) of the polymer. The elevated temperature serves to provide films prepared from such homopolymer coatings that exhibit sufficient adhesion of the film to the device, while preferably maintaining sufficient flexibility to resist film cracking upon expansion/contraction of the coated medical device. Certain films and coatings made from the copolymer compositions of the present invention provide these same physical and mechanical properties, or essentially the same properties, even when the maximum temperatures to which the coatings and films are exposed is less than about 100° C., and preferably less than about 65° C. This is particularly important when the coatings/films comprise pharmaceutical or therapeutic agents or drugs that are heat sensitive, e.g. subject to chemical or physical degradation or other heat-induced negative affects, or when coating heat sensitive substrates of medical devices, e.g., subject to heat-induced compositional or structural degradation.

A preferred fluoromonomer unit for the copolymer of the present invention is PVDF and its copolymer with hexafluoropropene, PVDF-HFP (polyvinylidene fluoride-co-hexafluoropropene). These polymers has been widely used in the medical device industry for a variety of applications. The key attributes of these polymers are that they provide almost the same chemical inertness as PTFE (poly tetrafluoroethylene or Teflon) but also are easily processable by a variety of commercial processes such as extrusion, molding, coatings and etc. Adding the copolymer hexafluoropropene to PVDF increases the toughness of the polymer and reduces the crystallinity. Also, PVDF or PVDF-HFP polymers have low coefficient of friction. The methods used to polymerize PVDF or PVDF-HFP polymers have been optimized to provide additive free, chemically and biologically stable polymers. A recent application pertains to use of these polymers as coatings for drug eluting stent (DES) products. These coatings contain the PVDF or PVDF-HFP polymer and a therapeutic drug to prevent restenosis.

In spite of these advantages, PVDF or PVDF-HFP based polymers have three major shortcomings. One is that the quality of adhesion obtained to standard surfaces such as stainless steel is poor. The quality of adhesion can be improved by adding a primer layer on substrate first, followed by the deposition of the PVDF based layer. If the drug is soluble in the primer layer it may accumulate in the primer layer over time thus compromising the ability of the polymer reservoir to release 100% of the drug. While primer coating method works, it is process intensive requiring two separate polymer applications to the stent. A second short coming is poor stent securement due to the low coefficient of friction of the stent coating. Addition of acrylate esters would increase stent securement. A third shortcoming is due to the poor solubility characteristics of therapeutic drugs in PVDF or PVDF-HFP polymers; it becomes difficult to obtain uniform drug release or tunable drug delivery. Others have attempted to improve control or delay release of drug is to use a thin top coat of polymer without drug. Inclusion of acrylate esters would increase the permeability of the drug through the polymer film. Manipulating the copolymer type and ratio should provide a convenient control of drug release. This control allows manipulation of the glass transition temperature of the resulting polymer composition. Increasing the mole % of acrylate or changing the nature of the acrylate to one having more organic character (for example, by changing the ester group from methyl to ethyl to propyl to butyl, etc.) will lower the crystallinity and glass transition temperature. Another way of doing so would be to incorporate more than one acrylate comonomer (for example use both a methyl and n-butyl acrylate). The addition of acrylates or methacrylates will also reduce the crystalline regions normally found in PVDF and provide adequate elasticity for the polymer to function well as a stent coating. This may eliminate the need for HFP copolymer in the fluoropolymer. Ideally a uniform daily dose of drug release is preferred for most of DES type applications ultimately releasing nearly 100% of the drug.

This disclosure aims at finding PVDF and/or HFP based compositions that provide a remedy to the above mentioned three shortcomings.

Acrylic based polymers are miscible with PVDF based polymers. The specific incorporation of acrylate, methacrylate, and/or other alkylacrylate ester segments within the PVDF and/or HFP polymer or PVDF-HFP copolymer which is the subject of this invention provides novel compositions of polymer stent coatings. The corresponding acrylic, methacrylic, and/or other alkylacrylic acids could also be incorporated for further adhesion enhancement. The resulting polymer composition then provides both good adhesion to variety of substrates, improved stent securement and also provides tunability of drug release. Typical substrates of interest for medical devices are: stainless steel and its alloys, nitinol and its alloys, platinum based compositions, cobalt alloys and etc. Typical drugs of interest for the drug-eluting stent application are paclitaxel, everolimus and etc. Importantly, the acrylate, methacrylate, and/or other alkylacrylate ester segments of the present invention are those having hydrophobic ester groups (denoted $R^1$ in the structures below). The use of hydrophobic acrylate monomers in the polymer compositions of the present invention results in polymers having greater contact angle with aqueous compositions and other compositions of high or relatively high polarity. Use of hydrophobic acrylates helps to minimize adhesion of the polymer composition to typical biomolecules (bioadhesion). Additionally, the polymer compositions of the present invention having hydrophobic acrylates are less tacky in medical implant uses in comparison to polymer compositions comprising hydrophilic monomers.

In some embodiments, the $R^1$ ester group may possess a polar or charged group provided that the side chain has a sufficiently lengthy aliphatic component to retain an overall hydrophobic character. Typically, a length of that aliphatic chain of at least 3 carbon atoms is sufficient to accomplish this end.

The acrylate components could be incorporated into a fluoropolymer in four different ways to create the composition of the present invention. While most of the specific examples below focus on vinylidenedifluoride, hexfluorpropene, or PVDF-HFP, it should be understood that other fluoromonomers may be used in the polymers or blends of the present invention.

The incorporation of acrylate comonomer into a vinylidene difluoride homopolymer allows one to decrease the crystallinity of and the elastic modulus of the resulting polymer composition. However, this also results in substantial increases in elongation of the resulting polymer as well. Incorporating one or more acylate monomer into a fluoropolymer (prefereably either vinylidene difluoride homopolymer or PVDF-co-HFP) allows one to one to decrease the crystallinity of and the elastic modulus substantial with lesser degrees of increase in elongation of the resulting polymer composition. Additionally, the incorporation of acrylate comonomer also provides a means to incorporate a polar moiety in the resulting polymer composition which can be used to modify the loading of pharmaceutical and/or therapeutic compositions into the polymer matrix.

Preferably, the level of acrylate in the final polymer is from 0-50 mole %, but may be greater than 50 mole %. In various embodiments, the level of acrylate in the final polymer can be 1 mole %, 2 mole %, 3 mole %, 4 mole %, 5 mole %, 6 mole %, 7 mole %, 8 mole %, 9 mole %, 10 mole %, 11 mole %, 22 mole %, 13 mole %, 14 mole %, 15 mole %, 16 mole %, 17 mole %, 18 mole %, 19 mole %, 20 mole %, 21 mole %, 22 mole %, 23 mole %, 24 mole %, 25 mole %, 26 mole %, 27 mole %, 28 mole %, 29 mole %, 30 mole %, 31 mole %, 32 mole %, 33 mole %, 34 mole %, 35 mole %, 36 mole %, 37 mole %, 38 mole %, 39 mole %, 40 mole %, 41 mole %, 42 mole %, 43 mole %, 44 mole %, 45 mole %, 46 mole %, 47 mole %, 48 mole %, 49 mole %, or 50 mole %. In other embodiments, the level of acrylate in the final polymer is 55 mole %, 60 mole %, 65 mole %, 70 mole %, 75 mole %, or 80 mole %. Preferably the range of the level of acrylate in the final polymer is from 1-50 mole %. Alternatively, the level of acrylate in the final polymer is from 10-50 mole %, 10-25 mole %, or 10-20 mole %. Alternatively, the level of acrylate in the final polymer is from 20-50 mole %. In other embodiments, the level of acrylate in the final polymer is from 25-50 mole %, or from 25-40 mole %. In other embodiments, the level of acrylate in the final polymer is from 30-50 mole %, or from 30-45 mole %, or from 30-40 mole %, or from 30-35 mole %.

Simple polymer blends: This includes mixing up to 50% by weight of polyacrylates, polymethacrylates, or other polyalkylacrylates, or their copolymers with PVDF and PVDF-HFP polymers. Polyacrylates and polymethacrylate based polymers are known to miscible with PVDF and PVDF-HFP copolymers. Blends of such polymers could yield single phase or bi phasic mixtures depending upon the fraction of each component within the blend. Blends are technologically simple to make and use to coat medical devices. Preferably, the blends of fluoropolymer (which can be a homopolymer, copolymer, or polymer having 3 or more different monomers) and polyacrylate (which can be a homopolymer, copolymer, or polymer having 3 or more different monomers) are blends in which the components are miscible with one another. The individual polymers of the blends may be random, block or graft copolymers.

Copolymers: This includes random copolymers of acrylic, methacrylic, or other alkylacrylic monomers with vinylidene fluoride or vinylidene fluoride+hexafluoropropene monomers. These can be made typically in suspension polymerization or solution polymerization or in supercritical $CO_2$ polymerization or perhaps ionic fluid media. The mole % of acrylate or methacrylate is preferably no higher than 50%, but may be greater than 50% depending on the desired physical and chemical properties. Preferably, the mole % of acrylate and the identity of the acrylate monomer unit(s) are varied to achieve a copolymer having a glass transition temperature of below 35° C. Alternatively, these parameters may be varied to achieve a copolymer having a glass transition temperature of below 30° C., below 25° C., below 20° C., below 15° C., below 10° C., below 5° C., or below 0° C. Broadly, it is preferable to keep the glass transition temperature of below body temperature (approximately 37° C.). Using hydroxy ethyl methacrylate type monomers could impart hydrophilic character to the coatings. Suspension polymerization is the preferred method since it uses fewer additives. However solution polymerization techniques could also be used but will have to be followed up with adequate cleaning processes including precipitation and drying.

Block copolymers: When PVDF and PVDF-HFP are produced by emulsion polymerization they contain ionic end-groups. These ionic end-groups can be used to initiate homo polymerization of acrylic, methacrylic, or other alkylacrylic monomers. Such polymerizations will yield ABA type block copolymers where segment A is the acrylic or methacrylic portion and segment B is the vinylidene fluoride or vinylidene fluoride-hexafluoropropene portion. Similarly using living free radical or cationic polymerizations a living mid-block of poly acrylate can be first made and then vinylidene fluoride or vinylidene fluoride and hexafluoropropene can be polymerized on the ends to produce the BAB block structure. Due to the compatibility of the two block materials, there may be no block phase separation observed. However, under certain processing conditions, the PVDF blocks may crystallize from the miscible acrylic-fluoropolymer phase.

Graft copolymers: Starting with PVDF or PVDF-HFP polymer acrylate, methacrylate or other alkylacrylate segments can be synthesized by abstracting a fluorine atom of the main polymer chain using ATRP (atom transfer radical polymerization using CuI and a ligand such as PMDETA or PEDETA) via a redox-halogen exchange reaction or other free radical initiator. Here, the fluorine sites on the PVDF or PVDF-HFP chain act as the initiating site to polymerize acrylate or methacrylate polymers. Typically copper based catalysts are employed to activate ATRP polymerizations. This could result in blocks of acrylate being added along the PVDF or PVDF-HFP backbone.

In all of the above cases, there may be one or more additional components. For example, in the blend embodiment, there may be one or more other polymers in the blend. Non-limiting examples include poly(lactic acid), or poly(vinylacetate). In the copolymer embodiments, there may be one or more additional monomer (thus copolymer herein encompasses terpolymers and higher polymers). Preferred examples include hydrophilic monomers such as those containing carboxy, amine, hydroxy, cyano, nitro, and other groups. When such monomers are present, the preferable range is less than 10 mole percent of the composition.

The acrylate monomers of the compositions of the present invention are hydrophobic acrylates. This is contrasted with hydrophilic acrylates which are those acrylates having polar functional groups such as carboxylate (—COOH), amine, alcohol, amide, nitro, cyano, etc. Such groups have a significant charge separation outside of the ester group of the acrylate. The preferred acrylate is characterized by the following general structure, which is defined herein as "formula I":

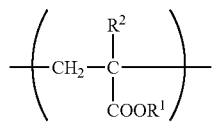

(I)

$R^1$ and $R^2$ can be the same or different and $R^1$ may be a $C_6$-$C_{10}$ aryl, a 5- to 12-membered heterocyclic group, $C_1$-$C_{10}$ alkyl, $C_2$-$C_{10}$ alkenyl, $C_2$-$C_{10}$ alkynyl, or $C_3$-$C_6$ cycloalkyl. $R^2$ may be a $C_6$-$C_{10}$ aryl, a 5- to 12-membered heterocyclic group, $C_2$-$C_{10}$ alkyl, $C_{10}$ alkyl, $C_2$-$C_{10}$ alkenyl, $C_2$-$C_{10}$ alkynyl, or $C_3$-$C_6$ cycloalkyl. Additionally, $R^2$ may also be hydrogen or an ester group (—$COOR^3$), wherein $R^3$ may be a $C_6$-$C_{10}$ aryl, a 5- to 12-membered heterocyclic group, $C_1$-$C_{10}$ alkyl, $C_2$-$C_{10}$ alkenyl, $C_2$-$C_{10}$ alkynyl, or $C_3$-$C_6$ cycloalkyl. In preferred embodiments, $R^2$ is hydrogen. In preferred embodiments, $R^2$ is hydrogen and $R^1$ is $C_1$-$C_{10}$ alkyl.

Non-limiting examples of a $C_1$-$C_{10}$ alkyl include, methyl, ethyl, propyl, isopropyl, butyl, (including all possible isomers isobutyl, sec-butyl, t-butyl), propyl (including all possible isomers thereof), pentyl (including all possible isomers thereof), hexyl (including all possible isomers thereof), heptyl (including all possible isomers thereof), octyl (including all possible isomers thereof), nonyl (including all possible isomers thereof), and decyl (including all possible isomers thereof). Non-limiting examples of $C_2$-$C_{10}$ alkenyl include, ethylenyl, propylenyl (including all possible isomers thereof), butylenyl (including all possible isomers thereof), pentylenyl (including all possible isomers thereof), hexylenyl (including all possible isomers thereof), heptylenyl (including all possible isomers thereof), octylenyl (including all possible isomers thereof), nonylenyl (including all possible isomers thereof), and decylenyl (including all possible isomers thereof). Non-limiting examples of $C_2$-$C_{10}$ alkynyl include ethynyl, propynyl (including all possible isomers thereof), butynyl (including all possible isomers thereof), pentynyl (including all possible isomers thereof), hexynyl (including all possible isomers thereof), heptynyl (including all possible isomers thereof), octynyl (including all possible isomers thereof), nonynyl (including all possible isomers thereof), and decynykl (including all possible isomers thereof). Non-limiting examples of $C_3$-$C_6$ cycloalkyl include cyclopropyl, cyclobutyl, cyclopentyl, and cyclohexyl. The $C_3$-$C_6$ cycloalkyl groups of the present invention may even include one or more sites of unsaturation such as, but not limited to cyclopropenyl, cyclobutenyl, cyclopentenyl, and cyclohexenyl. The $C_6$-$C_{10}$ aryl includes aryl groups having 6-10 ring atoms; the term "aryl" refers to monocyclic, bicyclic, and tricyclic ring systems having a total of six to ten ring members, wherein at least one ring in the system is aromatic and wherein each ring in the system contains 3 to 7 ring members. Aryl includes "heteroaryl", "heteroaralkyl", "heteroaralalkenyl", and "heteroaralalkynyl", which include one or more heteroatoms (atoms other than carbon). Non-limiting examples of $C_6$-$C_{10}$ aryl include phenyl, benzyl, tolyl, xylyl (including all possible isomers thereof), mesityl (including all possible isomers thereof), and naphthyl. Mixed combinations of the above examples are also within the scope of the invention wherein the polymer comprises more than one acrylate monomer.

Non-limiting examples of the types of polyacrylates which could be used for any of the above options include polymethacrylate (PMA), polymethylmethacrylate (PMMA), polyethylmethacrylate (PEMA), polybutylmethacrylate (PBMA), polyhexylmethacrylate (PHEMA), polybutacrylate (PBA), polyethacrylate (PEA), PAM (polyacrylamide) and others well known in the art. The individual acrylate monomer is the aforementioned polyacrylates represent non-limiting examples of acrylate monomers that can be used both in acrylate homopolymers and in copolymers having acrylate monomers and one or more non-acrylate monomers.

Other acrylate monomers used in the compositions of the present invention include acrylates having the following general structure, which is defined herein as "formula II":

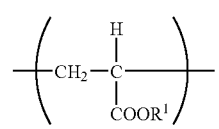

(II)

Non-limiting examples of compounds of formula II include polymethylacrylate (PMA), polyethacrylate (PEA), polypropylacrylate (PPA), polybutylacrylate (PBA), polyhexylacrylate (PHA), polyprop-1-ene-acrylate.

Other acrylate monomers used in the compositions of the present invention include methacrylates having the following general structure, which is defined herein as "formula III":

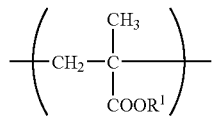
(III)

Non-limiting examples of compounds of formula III include poly(methyl methacrylate) (PMMA), poly(ethyl methacrylate) (PEMA), poly(propyl methacrylate) (PPMA), poly(butyl methacrylate) (PEMA), poly(prop-1-ene-methacrylate), etc.

Non-limiting examples of compounds of formula I include poly(methyl ethacrylate) (PMEA), poly(methyl butacrylate) (PMBA), poly(methyl pentacrylate) (PMPA), poly(ethyl ethacrylate) (PEEA), poly(propyl ethacrylate) (PPEA), poly(methyl prop-1-ene-ethacrylate), etc.

In formulas II and III, $R^1$ is the same as was described for formula I.

In the case of acrylates, the monomeric starting materials is an ester of acrylic acid:

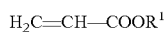

In the case of methacrylates, the monomeric starting material is an ester of methacrylic acid,

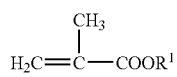

In the case of alkylacrylates, the monomeric starting material are esters of the various alkylacrylic acids,

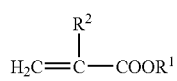

$R^1$ and $R^2$ are as have been earlier defined herein for each corresponding analogous formula. Homopolymerization of these species or copolymerization with fluoromonomers (most notably, vinylidene difluoride and/or hexafluoropropylene) involves polymerization across the terminal carbon-carbon double bond.

In addition, the inventors have found that other structures, similar to acrylates in their mechanism of homo- and co-polymerization, also produce improved polymer coatings. Unlike the acrylate, methacrylate and other alkylacrylate based systems, the non-fluorinated monomer of these other systems may have hydrophilic and/or hydrophobic functional groups.

In one embodiment, the non-fluorine-containing comonomer contains a carboxylic acid and ester function, with polymerization occurring across a carbon-carbon double bond in an analogous fashion as for the acrylate, methacrylate and other alkylacrylate based systems. Although m can be anywhere from 0-6, in some specific embodiments, m=4; in some other specific embodiments, m=5; while in other embodiments, m=6. The general structure of the staring material is provided below:

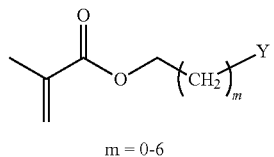

m = 0-6

In the above structure, Y may be —COOH, —NH$_2$, —SH, —OH, —Si(OCH$_3$)$_3$, and any of the following groups (with the bond to the left representing the linkage to the —(CH$_2$)$_m$— group):

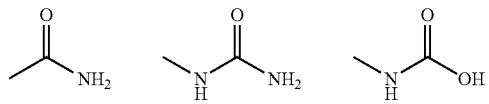

Polymerization of formula IV across the carbon-carbon double bond yields the following monomer unit within the polymer (the following general structure is defined herein as "formula IV"):

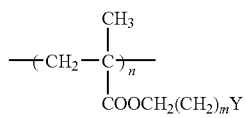
(IV)

Where n is 1 or more and Y are defined as above.

In another embodiment, the non-fluorine-containing co-monomer contains a carboxylic acid and ester function, with polymerization occurring across a carbon-carbon double bond in an analogous fashion as for the acrylate, methacrylate and other alkylacrylate based systems.

Other polymeric systems comprising the acrylate and fluoro monomers are also included in the present invention. Such systems include additional monomers. A non-limiting example of the staring material for use with one or more fluoro monomers and/or one or more acrylate monomers is provided below:

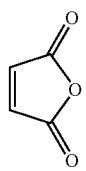

Polymerization across the ring double bond results in a monomer unit formed from the maleic anhydride structure. Such a monomer can be part of a copolymer or terpolymer having fluoro and acrylate monomers. Other similar structures, apparent to the skilled artisan are also included in the invention.

In other embodiments, the $R^1$ group of the ester group of the acrylate can contain zwitterionic side chains such as taurine and taurine-like structures.

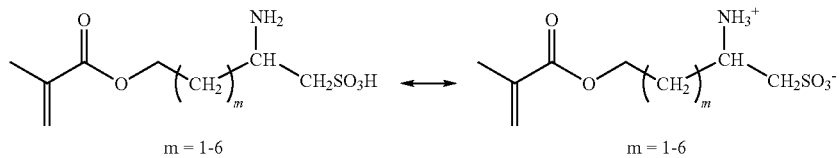

Polymerization of the above structures yields the following general structure, herein defined as "formula V":

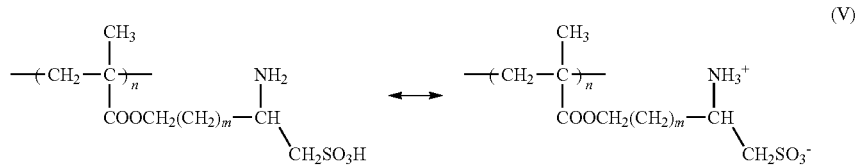

wherein n is 1 or more and m=1-6.

Other amino acids may also be used. Additionally, other charged groups may be used:

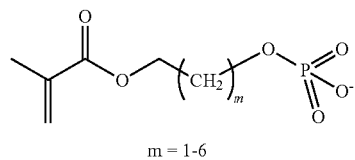

resulting in the following monomer unit (the following general structure herein defined as "formula VI"):

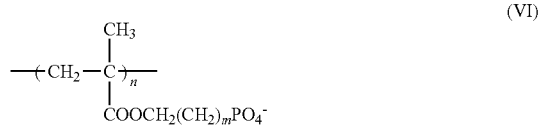

wherein n is 1 or more and m 1-6.

The copolymer of fluorinated monomers and hydrophilic monomers can form a coating optionally with a biobeneficial material. The combination can be mixed, blended, or coated in separate layers. The biobeneficial material useful in the coatings described herein can be a polymeric material or non-polymeric material. The biobeneficial material is preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent.

Examples of biobeneficial materials include, but are not limited to, polyethers such as poly(ethylene glycol); copoly (ether-esters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, block copolymers having flexible poly (ethylene glycol) and poly(butylene terephthalate) blocks (PEGT/PBT) including AB, ABA, BAB copolymers having such segments of PEG and PBT (e.g., poly(ethylene glycol)-block-poly(butyleneterephthalate)-block-poly(ethylene glycol) (PEG-PBT-PEG)), and combinations thereof. In some embodiments, the coating can exclude any one of the aforementioned polymers.

The polymeric compositions described herein may optionally include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombotic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-

(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin™ from Pharmacia & Upjohn, Peapack, N.J.), and mitomycin (e.g. Mutamycin™ from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, cholsterol-lowering drugs such as lovastatin and/or simvastatin from Merck & Co., Inc., Whitehouse Station, N.J., monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril from Bristol-Myers Squibb Co., Stamford, Conn.), cilazapril or lisinopril from Merck & Co., Inc., Whitehouse Station, N.J. An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

The implantable device upon which the inventive compositions may be used may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads. The device may be an orthopaedic implant such as a knee of hip implant. The underlying structure of the device can be of virtually any design. The device can be made of a metallic material or an alloy such as, but not limited to, cobalt chromium alloy, stainless steel (316L), high nitrogen stainless steel, but may also be non-metallic such as a polymeric material. Devices made from bioabsorbable or biostable polymers could also be used with the embodiments of the present invention. The device itself, such as a stent, can also be made from the described inventive polymers or polymer blends.

Exemplary Synthesis of PVDF-co-Butyl Acrylate Random Copolymer

The following example provides a synthetic method for PVDF-co-Butyl acrylate copolymer. The same method can be applied to make the range of polymers described herein, including those of Formulas I, II, and III. The acrylate starting material would be modified by the appropriate substitution of $R^1$ and $R^2$ groups. A typical reaction would include the use of a high pressure reactor that is rated to >2000 psi and equipped with maintaining temperatures up to 120° C. The following describes an effort to make PVDF-co-butyl acrylate inside a fumed hood with adequate air flow and nitrogen purging.

To a clean 500 mL reactor, 1 g of ammonium persulfate and 4 g of n-butyl acrylate are added. The reactor is nitrogen purged for 5 minutes. Vinylidene fluoride monomer is then added to the reactor until the pressure in the reactor is same as the pressure in the vinylidene fluoride monomer tank. Typically, about 40-60 g vinylidene fluoride monomer is added to the reactor with the reactor pressure at 350-400 psi. Nitrogen bubbled deionized water is then added to the reactor using a Waters 501 HPLC pump with 1/16 in stainless steel tubing. Water is pumped at 9 mL/min and as the reactor is filled with water the pressure inside starts to increase. In about 1 hour, about 400-440 mL of water is added to the reactor and the pressure inside gets to 500-600 psi. Then the reactor ports are closed and the contents are stirred at a high rpm to thoroughly disperse the contents in water. The temperature controller is set to 70° C. and the reactor is gently warmed to reach the set point in 1-2 hours. Once the set point is reached the pressure inside the reactor will be at 1200-1400 psi. The reactor is left at 70° C. and constant agitation for overnight.

The half of ammonium persulfate at 70° C. is such that within 10-16 hours or typically the next day morning the pressure inside the reactor reaches <50 psi indicating that the VDF monomer is polymerized. The contents of the reactor nitrogen purged to remove any unreacted monomer and then are emptied into a glass beaker. The reaction results a milky white suspension of polymer particles in water about 400 mL in volume. To this, at least 1-2 L of deionized water is added and the contents can be left standing overnight. The next day sediment is formed which is recovered by filtration and the filtrate could be further purified by water washes. Then the sediment is dried in a vacuum oven to result a powdery polymer residue. The identity of PVDF-co-BA can be confirmed by infrared spectroscopy, the carbonyl peak of butyl acrylate is present at approximately 1700 $cm^{-1}$.

This non-limiting example describes a general procedure. Variations can be made and are within the scope of the present invention. For the case of butyl acylate as the acrylate comonomer, the butyl acrylate content is preferably varied from 1-50%, although higher percentages could be used. Higher butyl acrylate contents could make the copolymer with vinylidene fluoride more tacky. The content of other acrylates could be varies according to the properties of the final product desired. Other initiators could be used such as from the family of peroxides, peroxycarbonates, and peroxidicarbonates along with the water soluble ones used in this report—ammonium persulfate. The polymerizations could be carried out in a solvent such as acetone, cyclohexanone, dimethyl formamide (DMF) and others instead of suspension polymerization.

Exemplary Synthesis of PVDF-co-HFP/Butyl Acrylate Graft Copolymer

A non-limiting example of a procedure for a graft copolymer follows. The resulting graft polymer has an n-butyl acrylate group emanating from the fluorine groups on PVDF-co-HFP polymer are described in this synthesis procedure.

A 100 mL glass flask is equipped with a thermocouple and a heating mantle along with a magnetic stir rod and a stir plate. PVDF-co-HFP polymer is first dissolved in 70/30 acetone cyclohexanone for a solution having about 5-15% solids. This solution is added to the 100 mL flask and nitrogen bubbled for 1 hour. Then ATRP catalysts Copper bromide and PMDETA are added to the PVDF-co-HFP solution. Nitrogen bubbling is maintained for another hour. Then butyl acrylate monomer stripped of its inhibitor is added to the 100 mL flask. Nitrogen purge is maintained on the head space through out the reaction. The contents of the flask are heated to 50° C. and the reaction was continued for 1 day.

After one day the contents of the flask are dissolved in excess acetone. This solution is precipitated into methanol and the precipitate is collected. The dissolution and precipitation is repeated one more time. The precipitate is dried on a vacuum oven. Upon inspection, it was found tacky to the touch. This indicates that the butyl acrylate polymerization has occurred with PVDF-co-HFP as the initiator.

One skilled in the art readily appreciates that the present invention is well adapted to carry out the objectives and obtain the ends and advantages mentioned as well as those inherent therein. Systems, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the claims.

What is claimed is:

1. A medical implant comprising a coating that comprises a copolymer composition, said copolymer composition comprising:
a fluoromonomer unit selected from the group consisting of vinylidene difluoride, hexafluoropropylene and combinations thereof; and
an acrylate monomer unit of the formula I,

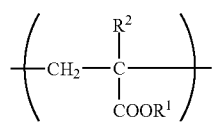

(I)

wherein $R^1$ is a $C_1$-$C_{10}$ alkyl and $R^2$ is H or $CH_3$.

2. The medical implant of claim 1, wherein the mole % of said acrylate monomer unit in the copolymer composition is 50% or lower.

3. The medical implant of claim 1, wherein the mole % of said acrylate monomer unit in the copolymer composition is selected from the group consisting of 10-20%, 10-50%, and 25-50%.

4. The medical implant of claim 1, wherein the copolymer composition has a glass transition temperature of less than 35° C.

5. The medical implant of claim 1, wherein the copolymer composition has a glass transition temperature of less than 20° C.

6. The medical implant of claim 1, wherein the copolymer composition comprises a random copolymer, a block copolymer, or a graft copolymer.

7. The medical implant of claim 1, wherein the acrylate monomer unit is selected from the group consisting of methylmethacrylate, ethylmethacrylate, butylmethacrylate, hexylmethacrylate, methacrylate, n-butylacrylate, ethylacrylate, and any combination thereof.

8. The medical implant of claim 1, further comprising a bioactive agent.

9. The medical implant of claim 8, wherein said bioactive agent is an antithrombotic agent.

10. The medical implant of claim 1, further comprising an additional monomer unit wherein said additional monomer unit is present at less than 10 mole % of the composition.

11. A medical implant comprising a coating that comprises a copolymer composition, said copolymer composition comprising:
a fluoromonomer unit selected from the group consisting of vinylidene difluoride, hexafluoropropylene and combinations thereof; and,
an acrylate monomer unit of formula V,

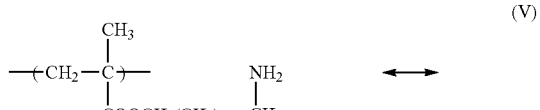

(V)

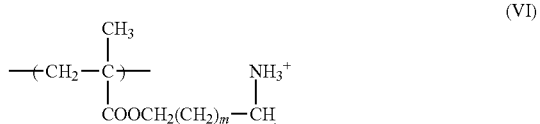

(VI)

formula VI,

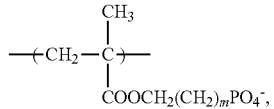

or a combination thereof, wherein m = 1-6.

12. The medical implant of claim 11, wherein the mole % of said acrylate monomer unit in the copolymer composition is 50% or lower.

13. The medical implant of claim 11, wherein the mole % of said acrylate monomer unit in the copolymer composition is selected from the group consisting of 10-20%, 10-50%, and 25-50%.

14. The medical implant of claim 11, having a glass transition temperature of less than 35° C.

15. The medical implant of claim 14, having a glass transition temperature of less than 20° C.

16. The medical implant of claim 11, wherein the copolymer composition comprises a random copolymer, a block copolymer, or a graft copolymer.

17. The medical implant of claim 11, further comprising a bioactive agent.

18. The medical implant of claim 17, wherein said bioactive agent is an antithrombotic agent.

19. The medical implant of claim 11, further comprising an additional monomer unit wherein said additional monomer unit is present at less than 10 mole % of the composition.

20. A medical implant comprising a coating that comprises a polymer blend composition, said copolymer composition comprising:
   a fluoromonomer unit selected from the group consisting of vinylidene difluoride, hexafluoropropylene and combinations thereof; and
   a polyacrylate having a monomer unit of the formula I,

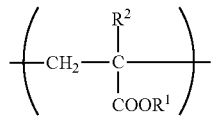

(I)

wherein $R^1$ is a $C_1$-$C_{10}$ alkyl and $R^2$ is H or $CH_3$.

21. The medical implant of claim 20, wherein said polymer blend further comprises a third polymer, said third polymer being substantially free of fluoromonomers and acrylate monomers.

22. The medical implant of claim 1, wherein $R^1$ is other than methyl.

23. The medical implant of claim 22, wherein said copolymer composition comprises a block copolymer or a graft copolymer.

24. The medical implant of claim 1, wherein said copolymer composition comprises a block copolymer or a graft copolymer.

25. The medical implant of claim 22, wherein the an acrylate monomer unit is of formula V,

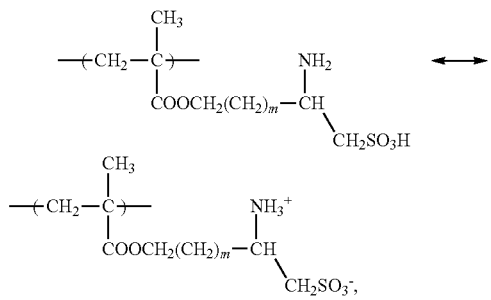

(V)

and wherein m = 1-6.

26. The medical implant of claim 1, wherein said copolymer composition does not comprise an additional acrylate monomer unit having a polar functional group selected from a carboxylate group, an amine group, an alcohol group, and amide group, a nitro group and a cyano group.

27. The medical implant of claim 1, wherein said copolymer composition comprises more than one type of acrylate monomer unit.

28. The medical implant of claim 1, selected from stents, stent-grafts, grafts, artificial heart valves, cerebrospinal fluid shunts, pacemaker electrodes, and endocardial leads.

29. The medical implant of claim 22, wherein said copolymer composition does not comprise an additional acrylate monomer unit having a polar functional group selected from a carboxylate group, an amine group, an alcohol group, and amide group, a nitro group and a cyano group.

30. The medical implant of claim 22, wherein said copolymer composition comprises more than one type of acrylate monomer unit.

31. The medical implant of claim 22, selected from stents, stent-grafts, grafts, artificial heart valves, cerebrospinal fluid shunts, pacemaker electrodes, and endocardial leads.

* * * * *

UNITED STATES PATENT AND TRADEMARK OFFICE
CERTIFICATE OF CORRECTION

PATENT NO. : 8,475,844 B2  
APPLICATION NO. : 12/424946  
DATED : July 2, 2013  
INVENTOR(S) : Gordon Kocur et al.

It is certified that error appears in the above-identified patent and that said Letters Patent is hereby corrected as shown below:

In the Claims:

Col. 20, line 1, after "claim" change "22" to --11--

Signed and Sealed this  
Third Day of September, 2013

Teresa Stanek Rea  
*Acting Director of the United States Patent and Trademark Office*